United States Patent [19]

Boron

[11] 4,118,988
[45] Oct. 10, 1978

[54] BOTTOM FILL SAMPLING APPARATUS

[75] Inventor: Joseph J. Boron, Medina, Ohio

[73] Assignee: Rossborough Manufacturing Co., Cleveland, Ohio

[21] Appl. No.: 826,186

[22] Filed: Aug. 19, 1977

[51] Int. Cl.² ............................................. G01N 1/12
[52] U.S. Cl. ............................................. 73/425.4 R
[58] Field of Search ..................... 73/425.4 R, DIG. 9

[56] References Cited

U.S. PATENT DOCUMENTS

| 3,481,201 | 12/1969 | Falk | 73/425.4 R |
|---|---|---|---|
| 3,656,350 | 5/1970 | Collins | 73/DIG. 9 |
| 4,048,857 | 9/1977 | Bardenhever | 73/425.4 R |

Primary Examiner—S. Clement Swisher
Attorney, Agent, or Firm—Fay & Sharpe

[57] ABSTRACT

The specification and drawings disclose an apparatus for taking samples of molten metal. The preferred embodiment comprises a housing enclosing a body defining a material flow path and a sample chamber. The material flow path and chamber are configured such that when the device is oriented in its position of use the material flowing into the flow path enters the housing and body from a position on a plane at about the top of said mold chamber, courses through the flow path to a position below said chamber and enters said chamber from said lower area. The body further comprises a conduit extending upwardly from said chamber and exiting the body at its top into a slag and shrink chamber.

1 Claim, 6 Drawing Figures

4,118,988

BOTTOM FILL SAMPLING APPARATUS

BACKGROUND OF THE INVENTION

1. Field of the Invention

This invention relates to immersion apparatus for obtaining a sample of molten metal. Such apparatus is generally to be found in the U.S. Patent and Trademark Office subclasses relating to measuring and testing, sampler, and toller implements.

2. Description of the Prior Art

Metal sampling apparatus of the prior art are generally of two types: those which may be immersed in a bath of metal to obtain a sample and those which may be inserted into a stream of molten metal. The present invention relates specifically to a type of device that is to be immersed for obtaining a sample. In the past, means have been employed including variously configured dippers, suction-type apparatus, tubes and the like. Of these examples, the most common were those that were simply dipped into the bath to obtain a sample. Some had side entry ports which necessarily imposed a limit on a degree of filling the sampler could achieve. This, of course, posed a problem in obtaining a uniform sample for subsequent analysis. In some of the bottom fill apparatus that have previously been used, a degree of difficulty has also been encountered in obtaining uniform samples. This is due to the fact that certain amount of material runout has been experienced due to the location of the entry port at the commencement of the material flow path through the device.

SUMMARY OF THE INVENTION

The subject invention provides an improved construction for a device for taking samples of molten metal. Sampling devices formed in accordance with the invention provide a better sample of molten metal and are more efficient than prior devices. Further, the subject invention overcomes problems previously encountered in obtaining uniform samples. Additionally, due to the configuration of the path, uniform samples can be obtained without undesirable shrinking and an area has been provided for the accumulation of undesirable slag and waste that often contaminated the samples produced by prior art devices.

Improvements have also been made in the protective cap guarding the ingress of the flow path into the sample cavity.

In particular, the invention contemplates an assembly which includes a core sand body defining a mold cavity. The core sand body is normally contained within a housing assembly, which is mounted on a lance in a conventional manner.

In addition to the mold cavity, the core sand body further defines a material flow path entering the body after coming through the side wall of the housing assembly. The flow path is normally capped at its outer extremity with a covering having a chemical analysis substantially similar to that of the desired final analysis of the molten metal being sampled. The flow path and mold chambers are so aligned that when the sampling apparatus is oriented to its position of use the entrance of the flow path lies near the top or slightly above a transverse plane drawn across the top of the sample chamber, and the exit of the flow path communicates with the chamber at the bottom of the chamber. The core sand body further defines metal egress channels which lead up and away from the mold chamber when the assembly is oriented into its position of use. These channels normally exit into a waste and shrink receptacle which accommodates any impurities encountered with the first portion of sample that enters the sampling apparatus. The waste chamber further accommodates shrinkage of the sample and is discardable so that the sample itself is fully and uniformly formed.

More specific aspects of the invention contemplate that the core sand mold will provide for the inclusion of chill discs, a pin sample and appropriate sample-venting means.

Accordingly, the primary object of the invention is the provision of an improved apparatus for taking samples from a bath of molten metal.

Another object is the provision of an apparatus of the type described wherein the samples obtained are substantially free of objectionable shrinkage. Another object is the provision of a flow path inlet port lying essentially above the mold cavity when the sampling apparatus is oriented to its position of use so that the cavity and pin sample tube, if one is employed, communicate with the flow path at their lower end thus providing a bottom fill. A still further object of the invention is the provision of a flow path entrance protecting cap comprised essentially of material substantially simulating in chemical analysis the desired final analysis of the molten metal being sampled.

Yet another object of the invention is to provide a sample that can be analyzed in a laboratory with a minimum of sample preparation.

The above and other objects and advantages will become more readily apparent when the following description is read in conjunction with the accompanying drawings.

DESCRIPTION OF THE PREFERRED EMBODIMENT OF THE INVENTION

Figure 1:
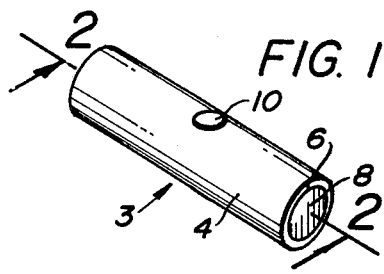
FIG. 1 is a perspective view of the sampling apparatus.

Referring now more particularly to the drawings wherein the showings are for the purpose of illustrating preferred embodiments of the invention only, and not for the purpose of limiting same, FIG. 1 shows a sampling device 3 formed in accordance with the invention. An outer housing 4 is provided with an open end 6 into which a core sand mold 8 is positioned. Container or housing 4 also is supplied with an apperture 10 through which molten metal enters the sampling apparatus.

Figure 3:
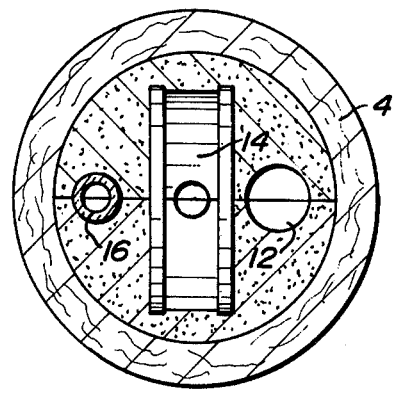
FIG. 3 is a complete transverse cross-sectional view taken in the area of line 3—3 of FIG. 2.
Figure 4:
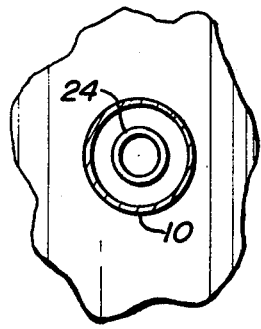
FIG. 4 is a view taken along line 4—4 of FIG. 2.
Figure 2:
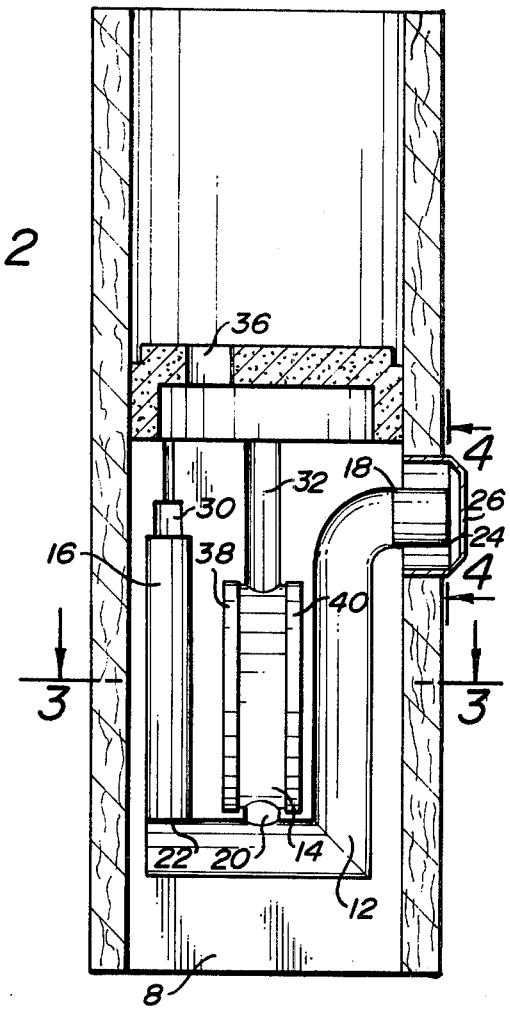
FIG. 2 is an enlarged cross-sectional view taken along line 2—2 of FIG. 1.

FIGS. 2, 3, and 4 best illustrate the details of the preferred embodiment of the sampling apparatus 3.

In general, the core sand mold 8 defines a flow path 12 and a mold cavity 14. In the showing of FIG. 2 there is also provided a pin sample cavity 16. The apparatus, as illustrated in FIG. 2, is shown oriented generally in its position of use, although it is well understood that when taking samples from a molten metal bath the sampling apparatus is generally secured to a lance member and often enters the bath at somewhat of an angle due to the positioning of the operator.

Referring still to FIG. 2, it will be seen that the flow path enters the core sand mold at point 18 which is substantially above the top of the mold chamber. The flow path continues to point 20 where it enters the mold chamber at a point below said chamber. This bottom fill feature is also true of the entrance to the pin sample chamber 22. At the point where the flow path enters the housing assembly, there is provided a ceramic sleeve 24 which serves to protect the housing. The entrance terminus of the flow path is normally protected by a cap 26 which is designed of material substantially similar in chemical analysis to that of the desired final analysis of the molten metal being sampled. This adaptation is particularly useful when testing high-alloy type steels.

It is also seen in FIG. 2 that the core sand defines outlet ports above both the pin sample chamber and the disc sample cavity at points 30 and 32, respectively. These vents or channels are exited into a waste receptacle 36.

It will be seen that the metal flowing into the flow path and then into the mold chambers out the exit tubes 30 and 32 and into the waste receptacle 36 will be the metal that first enters the sampling device. This metal is normally the most contaminated and, consequently, it is undesirable to have in the finished sample which is going to be used for analysis. Another feature of the waste receptacle is that shrinkage takes place at this point upon cooling the sample thus giving uniform and fully shaped pin samples and disc samples.

It will be noted also that slots are provided for the use of chill discs if this is desired at points 38 and 40.

Figure 5:
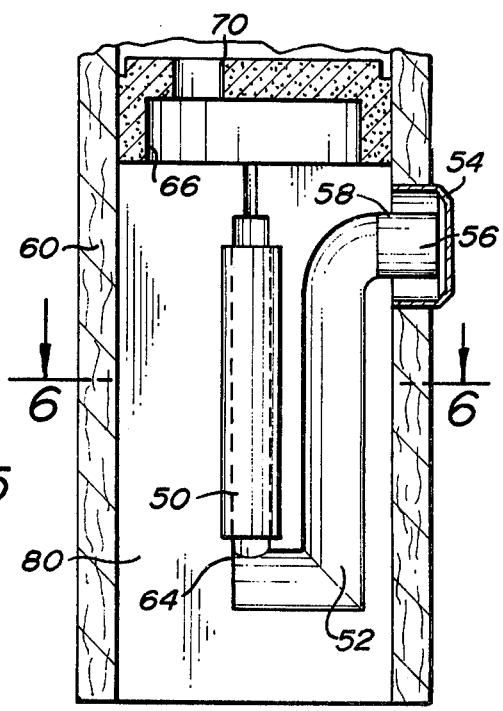
FIG. 5 is a longitudinal cross-sectional view of an alternative embodiment of the invention.

Referring now to FIG. 5, an alternative embodiment of the invention is shown in which the mold defines only a pin sample chamber 50. Similar, however, to the embodiment shown in FIGS. 1 through 4, the entrance to the flow path 52 lies essentially at or above the upper most limit of the pin sample chamber. The flow path entrance is also protected by a cap 54 and the initial portion of the path may be provided with a ceramic sleeve 56 which can be cemented at point 58 into the housing assembly 60. It is seen that molten metal entering the sample apparatus flows along flow path 52 after entering through the side of the housing and exits into the pin sample chamber at point 64. The material then flows up through the chamber and fills a waste receptacle 66 which is vented into the remainder of the housing at point 70. As with the embodiment shown in FIGS. 1 through 4, shrinkage is thus minimized in the area of the sampler which is used to form the sample which is actually going to be used for testing purposes.

Figure 6:
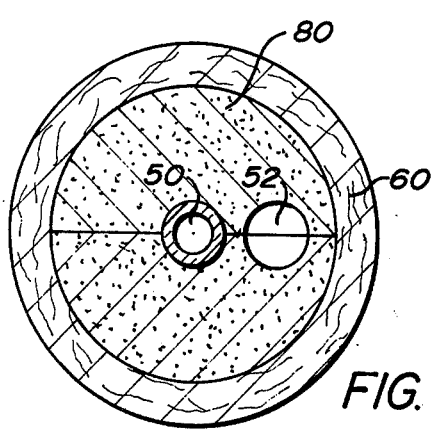
FIG. 6 is a complete cross-sectional view taken generally along line 6—6 of FIG. 5.

It may also be desirable in the embodiment of FIGS. 5 and 6 to use s protective cap 54 which is made of material conforming to that of the expected analysis of the melt. The cap, or protective member, burns off when the apparatus is used to allow entrance of metal into the sampler. It will be appreciated that the mold body 80 is shown as being made from core sand, although other materials are certainly capable of use within the spirit of the instant invention.

The invention has been described in detail sufficiently to enable one of ordinary skill in the art to make and use the same. It is obvious that modifications and alterations in the preferred embodiments will occur to others upon a reading and understanding of the specification. All such alterations and modifications are to be considered as part of the invention insofar as they come within the scope of the appended claims.

What is claimed is:

1. An apparatus for taking a sample of molten metal comprising:
   a housing adapted to be releasably secured to a lance;
   a body within the housing defining a mold cavity;
   said body and housing defining a molten metal flow path having an entrance and an exit, said body further defining a waste receptacle in communication with said cavity;
   a protective member over the entrance of said flow path, said member being comprised of material substantially similar in chemical analysis to that of the desired final analysis of the molten metal being sampled;
   said flow path entering said body and housing from the side and communicating with said mold cavity at the lower end thereof when said apparatus is oriented in its position of use.

* * * * *